United States Patent [19]

Ranade

[11] Patent Number: 4,482,732
[45] Date of Patent: Nov. 13, 1984

[54] PROCESS OF MANUFACTURING DIARYL ESTERS OF DICARBOXYLIC ACIDS

[75] Inventor: Gautam R. Ranade, Grand Island, N.Y.

[73] Assignee: Occidental Chemical Corporation, Niagara Falls, N.Y.

[21] Appl. No.: 422,793

[22] Filed: Sep. 24, 1982

[51] Int. Cl.³ .............................................. C07C 67/08
[52] U.S. Cl. .............................. 560/86; 203/DIG. 6; 260/455 R; 560/11; 560/18; 560/21; 560/37; 560/52; 560/73; 560/85; 568/15
[58] Field of Search ....................... 560/11, 18, 21, 37, 560/52, 73, 85, 86, 204; 568/15; 260/455 R; 203/DIG. 6

[56] References Cited

U.S. PATENT DOCUMENTS

| | | |
|---|---|---|
| 3,356,712 | 12/1967 | Renckhoff et al. ................. 560/86 |
| 3,389,164 | 6/1968 | Renckhoff et al. ................. 560/86 |
| 3,413,336 | 11/1968 | Hulsmann et al. ................. 560/86 |
| 3,471,549 | 10/1969 | Hulsmann et al. ................. 560/86 |
| 3,772,389 | 11/1973 | Lowrance ........................... 560/86 |

Primary Examiner—Natalie Trousof
Assistant Examiner—Vera C. Clarke
Attorney, Agent, or Firm—James F. Tao

[57] ABSTRACT

An improved process for preparing diaryl esters of dicarboxylic acids is disclosed, in which the esterification reaction is optimized by removing water and other by-products of the reaction according to a predetermined pattern. The removal of water and other by-products of the esterification reaction is most easily carried out by a distillation means, and the rate of removal is controlled by varying the reflux ratio in the distillation means during the course of the esterification reaction. The diaryl esters so prepared are useful in making linear polyesters.

18 Claims, 1 Drawing Figure

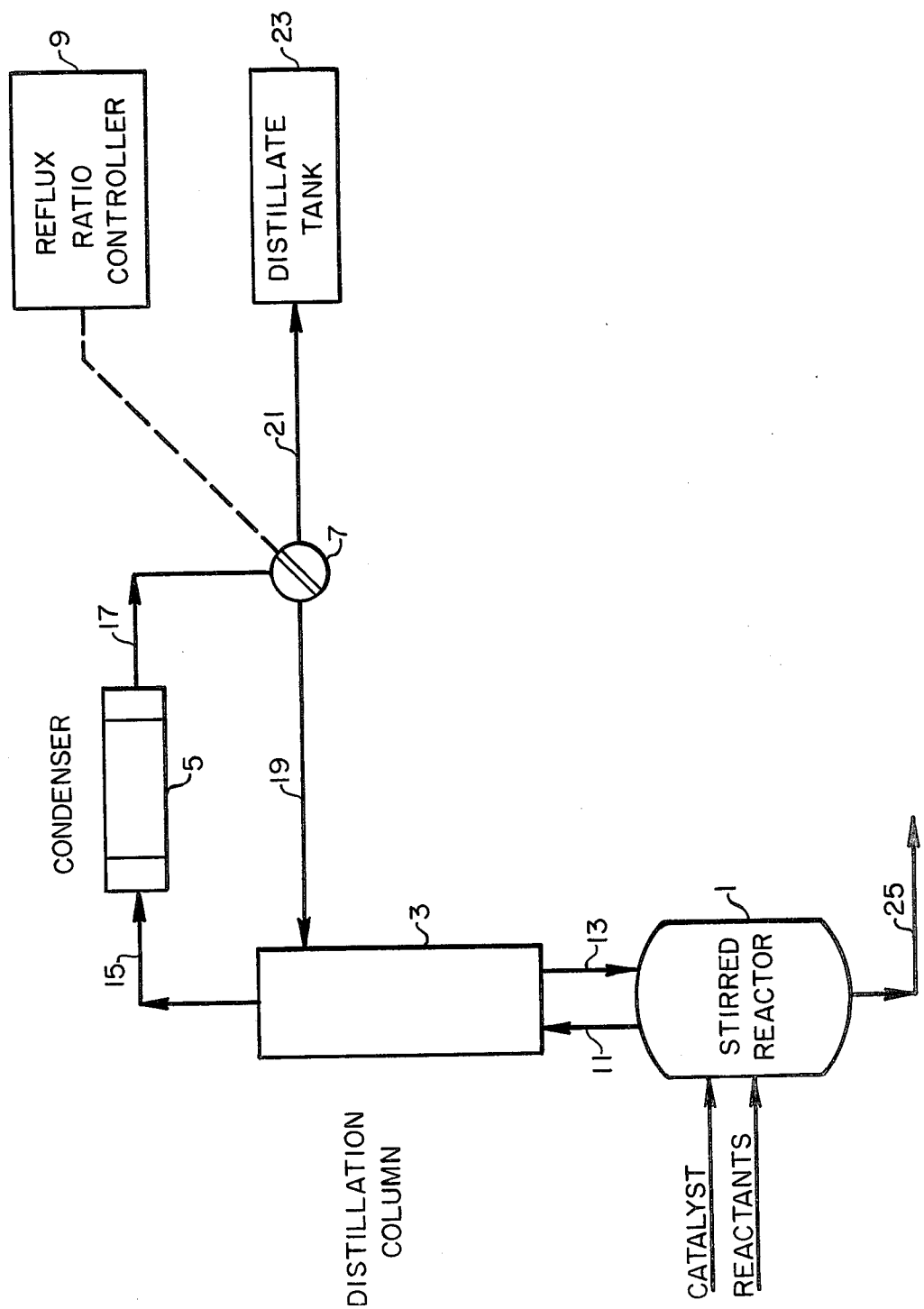

PROCESS OF MANUFACTURING DIARYL ESTERS OF DICARBOXYLIC ACIDS

BACKGROUND OF THE INVENTION AND PRIOR ART STATEMENT

This invention relates to an improved process for making esters. More particularly, the invention relates to an economical and efficient process for accelerating the rate of esterification in which dicarboxylic acids or their esters and monohydroxy aromatic compounds are reacted to form esters.

Linear polyesters which are essentially the product of reaction of a bisphenol and dicarboxylic acids are important thermoplastic materials due to their excellent performance at high temperatures. It is known to produce such linear polyesters by first reacting at least one dicarboxylic acid with a monohydroxy aromatic compound to form a diaryl ester of the dicarboxylic acid, and then carry out a transesterification polymerization between the diaryl ester and a bisphenol. See, e.g., British Pat. No. 924,607 and U.S. Pat. Nos. 4,255,555 and 4,319,017. However, those references are primarily concerned with transesterification reaction for preparing the linear polyesters.

Significant commercial interest in recent years has developed in the field of phenolic esters of aromatic dicarboxylic acids, such as diphenyl isophthalate and diphenyl terephthalate, due to their use in many processes. For example, mixtures of diphenyl isophthalate and diphenyl terephthalate can be reacted by melt polycondensation with 4,4'-(1-methyl-ethylidene) bis(phenol) to produce aromatic polyesters or polyarylates. Diphenyl phthalates can also be reacted with primary amines in a solvent to make polyamides. Likewise, 3,3'-diaminobenzidene may be condensed with various diphenyl esters to form polybenzimidazoles.

The prior art processes for preparing the diaryl esters suffer from a nubmer of disadvantages. To obtain a degree of esterification in excess of 90%, which is demanded by the economics of the processes, the prior art processes require lengthy reaction times. Diaryl esters substantially free of dicarboxylic acid may also be required for the production of high quality linear polyesters. Other disadvantages include a requirement for high reaction temperatures, i.e. in the range of 280°-300° C. Such relatively high temperatures not only consume more energy than reactions conducted at lower temperatures, but they also result in a darker colored product which may be contaminated with by-products from side reactions. Other prior art processes also utilize pressures in excess of 100 psig and approaching 200 psig, which is again more costly and increases safety hazards.

U.S. Pat. No. 4,124,566 discloses a process for preparing polyesters in which the first step is the esterification of a difunctional carboxylic acid with an aromatic monohydroxy compound and an aliphatic diol and/or a dihydroxybenzene. The esterification reaction is to be performed in the presence of an aromatic hydrocarbon medium. This disclosure of the use of a small portion of aromatic esters as solvent for the reaction as well as the use of an azeotrope, including aromatic hydrocarbons such as ethyl benzene, affords some relief from lengthy reaction cycles and low conversion rates. However, the addition of the aromatic esters in the esterification reaction mixture reduces the volume available for the reaction and, consequently, reduces yield per batch. The addition of an azeotropic agent also dilutes the reaction mixture, and it may adversely affect the solubility of the dicarboxylic acid in the mixture. The use of an azeotropic agent such as ethyl benzene or xylene also increases the potential for fire and explosion, and the added danger of environmental health hazards to workers exposed to the atmosphere. Thus, the use of such aromatic hydrocarbons requires careful monitoring and treatment to prevent contamination of the environment. Accordingly, there is a need for an improved process for making diaryl esters of dicarboxylic acids.

It is, therefore, an object of the invention to provide improved process for making diaryl esters of dicarboxylic acids.

It is another object of the present invention to provide an economical and environmentally safe process for making diaryl esters which permits relatively short reaction times and high conversion rates while operating at relatively low reaction temperatures and pressures.

These and other objects of the invention can be gathered from the following disclosure.

SUMMARY OF THE INVENTION

In accordance with the present invention, there is provided a process for the esterification of at least one dicarboxylic acid with a monohydroxy aromatic compound, in which the dicarboxylic acid is represented by the formula:

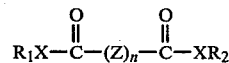

in which X is oxygen or sulfur, Z is alkylene, —Ar— or —Ar—Y—Ar— where Ar is aromatic, Y is alkylene of 1 to 10 carbon atoms, haloalkylene, —O—, —SO—, —SO$_2$—, —SO$_3$—, —CO—,

or GN=, and G is alkyl, haloalkyl, aryl, haloaryl, alkylaryl, haloalkylaryl, arylalkyl, haloarylalkyl, cycloalkyl and halocycloalkyl, n is 0 or 1, and R$_1$ and R$_2$ are independently selected from the group consisting of hydrogen and lower alkyl. The esterification reaction is carried out at a temperature between about 220° C. and about 300° C., preferably in the presence of a catalyst, while continuously removing a by-product of the esterification reaction comprising water and/or lower alkyl alcohol(s). Surprisingly, the applicant has found that the esterification reaction can be conducted at a relatively low temperature and yet achieve high conversion rates over short reaction times by the use of a distillation means to remove water or alcoholic by-products of the reaction in which the reflux ratio is varied during the course of the esterification reaction according to a predetermined pattern. The lower reaction temperatures made possible by the present invention result in better ester product quality and less by-products from side reactions. Generally, the reflux ratio should be increased as the esterification reaction proceeds towards completion. Advantageously, the reflux ratio is varied between a value of 1 and 20, and preferably between 2 and 15.

BRIEF DESCRIPTION OF THE DRAWING

In the drawing, a simple reactor system for carrying out the esterification reaction in accordance with the present invention is shown. A stirred reactor vessel 1 equipped with a distillation means 3 and condenser means 5 is operated with a reflux splitter 7, which is controlled by a reflux ratio controller 9. In operation, a charge of the reactants made of a mixture of the dicarboxylic acid(s) and the monohydroxy aromatic compound is charged into the reaction vessel 1 through inlet means (not shown). Advantageously, a catalyst is also charged into the reaction vessel 1 to assist the esterification reaction. Preferably, the reaction vessel 1 is equipped with a heating means and a temperature sensing means (both not shown). The heating means may be controlled in conjuction with the temperature sensing means to maintain the mixture within reaction vessel 1 at the predetermined temperature. As the esterification reaction proceeds, water and/or alcoholic by-products are produced in reaction vessel 1 and are vaporized at the reaction temperature and passed to the distillation means 9 through connecting means schematically represented by line 11. The return from distillation means to reaction vessel 1 is schematically represented by line 13. Distillation means 3 may be any of the known distillation devices, for example, bubble cap tray columns or packed towers. The overhead 15 from distillation means 9 is conducted to condenser means 5 and cooled there by a cooling medium such as water into a liquid condensate stream 17. Condensate 17 is split into two streams by a reflux splitter 7, which is controlled by the reflux ratio controller 9. The condensate stream 17 is split into a liquid return stream 19 and a distillate stream 21. The distillate stream 21 is passed to a distillate tank 23 for storage. The liquid return stream 19 is passed back to the top of the distillation means 9. Using the letter L to denote the moles of liquid return stream 19 and D to represent the moles of distillate stream 21, the Reflux Ratio is defined as the fraction L/D. The diaryl esters produced, together with unreacted reactants, are withdrawn from the reaction vessel 1 1 through line 25.

DETAILED DESCRIPTION OF THE INVENTION

As indicated above, the present invention provides an improved process for preparing diaryl esters, which are useful in the preparation of linear polyesters, by the reaction of at least one dicarboxylic acid or its ester with a monohydroxy aromatic compound. The dicarboxylic acids which are useful in the process of the invention are known and they can be represented by the formula:

$$R_1X-\overset{O}{\underset{\|}{C}}-(Z)_n-\overset{O}{\underset{\|}{C}}-XR_2$$

in which X is oxygen or sulfur, Z is alkylene, —Ar— or —Ar—Y—Ar— where Ar is aromatic, Y is alkylene of 1 to 10 carbon atoms, haloalkylene, —O—, —SO—, —SO$_2$—, —SO$_3$—, —CO—,

or GN=, and G is alkyl, haloalkyl, aryl, haloaryl, alkylaryl, haloalkylaryl, arylalkyl, haloarylalkyl, cycloalkyl and halocycloalkyl, n is 0 or 1, and $R_1$ and $R_2$ are independently selected from the group consisting of hydrogen and lower alkyl. Examples of aromatic and aliphatic dicarboxylic acids are disclosed in U.S. Pat. No. 4,126,602, and they include: aromatic dicarboxylic acids such as phthalic acid, isophthalic acid, terephthalic acid, bis(4-carboxyl)-diphenyl, bis(4-carboxyphenyl)-ether, bis(4-carboxyphenyl)-sulfone, bis(4-carboxyphenyl-carbonyl, bis(4-carboxyphenyl)-methane, bis(4-carboxyphenyl)-dichloromethane, 1,2- and 1,1-bis(4-carboxyphenyl)-ethane, 1,2- and 2,2-bis(4-carboxyphenyl)-propane, 1,2- and 2,2-bis(3-carboxyphenyl)-propane, 2,2-bis(4-carboxyphenyl)-1,1-dimethyl propane, 1,1- and 2,2-bis(4-carboxyphenyl)-butane, 1,1- and 2,2-bis(4-carboxyphenyl-pentane, 3,3-bis-(4-carboxyphenyl)-heptane, 3,3-bis(3-carboxyphenyl)-heptane; and aliphatic acids such as oxalic acid, adipic acid, succinic acid, malonic acid, sebacic acid, glutaric acid, azelaic, suberic acid and the like. Isophthalic acid and terephthalic acid are the preferred dicarboxylic acids for use in the process of the present invention, due to their easy availability and low cost. More preferably, the dicarboxylic acid employed in the esterification reaction comprises a mixture of about 60 to about 100 mole percent isophthalic acid and about 40 to about 0 mole percent terephthalic acid. Most preferably, the dicarboxylic acid component is made of a mixture of about 75 to about 85 mole percent isophthalic acid and about 25 to about 15 mole percent terephthalic acid.

The monohydroxy aromatic compounds for use in the process in the present invention is also known. Generally, they may be of the benzene or naphthalene series containing 6 to 20 carbon atoms. Examples of such monohydroxy aromatic compounds include phenol, o-, m-, or p-cresol, xylenol, a halophenol such as p-chlorophenol, 3,5-dibromophenol, a nitrophenol such as o-, m- or p-nitrophenol, 1-naphthol, 2-naphthol, 1-hydroxy-4-methyl naphthlene, and the like.

The dicarboxylic acid useful in the reaction of the present process include both aliphatic and aromatic acids as well as their respective esters. The rate of conversion may be enhanced when using mixtures of the acids or esters by increasing the proportions of the more soluble acid or ester in monohydroxy aromatic compounds over the less soluble acid or ester. In determining the exact proportion of acids to be used, consideration should be given to the properties of the esters produced and the effect they may have on the linear polyesters produced therefrom. When using mixtures of isophthalic and terephthalic acids, normally the isophthalic acid content will be increased up to the point where no significant change in polymer properties or processing characteristics are observed.

A molar excess of monohydroxy aromatic compound is preferably used in the reaction with the dicarboxylic acid to facilitate the completion of the esterification reaction. Although a molar ratio of the monohydroxy aromatic compound to the dicarboxylic acid of about 2:1 may be used, it is preferred that such molar ratio be from about 3:1 to about 10:1. More preferably, such molar ratio employed should be from about 4:1 to about 8:1.

The temperature to be employed in esterification process of the invention may be varied. Generally, temperatures should be between about 220° to 300° C. Most preferably, the temperature should be between about 235° C. to about 255° C. The pressure employed in the present process is determined by the temperature, the particular reactants employed, and other operating conditions. Generally, the pressure in the reaction vessel is substantially below 100 psig. Due to the relative moledular weights of water and the monohydroxy aromatic compound and their vapor pressures, a small amount of water in the reactants may cause the initial pressure in the reactor to be somewhat higher than indicated herein.

As indicated above, a catalyst is preferably used in the esterification reaction. These catalysts are known in the art. See, e.g., U.S. Pat. No. 4,124,566. Examples of the catalysts are elemental metals such as sodium, potassium, lithium, calcium, magnesium, barium, tin, strontium, zinc, iron, aluminum, cobalt, lead, nickel, titanium, magnesium, antimony or arsenic, and compounds of these metals such as their oxides, hydrides, hydroxides, halides, inorganic acid salts, organic acid salts, complex salts, double salts, alcoholates, or phenolates. Of these, titanium compounds such as titanium tetrabutoxide, titanium oxalate or titanium oxide, tin compounds such as dibutyltin oxide, antimony compounds such as antimony trioxide, and lead compounds such as lead oxide are preferred. I have found that organic titanium compounds, such as certain aliphatic esters of ortho titanic acid, are especially effective catalysts. Examples of aliphatic esters of ortho titanic acids include tetrabutyl titanate, tetraisopropyl titanate or tetraoctylene glycol titanate. Some of these organic titanium catalysts are available from the duPont Company under its trademark Tyzor. The amount of the catalyst to be used is also known in the art, and it is usually between about 0.001 to about 5 mole percent based on the amount of the dicarboxylic acid employed.

In the process of the present invention, the reflux ratio is varied during the course of the esterification reaction according to a predetermined pattern. The esterification process according to the invention may be carried out, in its simplest form, in a batch-wise manner as illustrated in the drawing, or it may be carried out in a more or less continuous manner, by having a plurality of reactors operating in stages. The reaction also may be carried out in a modified batch manner, such as by intermittantly adding the monohydroxy aromatic compound to the reactor in the earlier part of the reaction period. Referring to the batchwise operation, at the beginning of the esterification reaction, water or alcoholic by-products are produced quickly or in larger quantities per unit of time. These products of the esterification reaction are advantageously removed from the reactor system to drive the esterification reaction towards completion. Accordingly, the reflux ratio should be small at the beginning of the esterification reaction to maximize the removal of water or alcoholic by-products. Thus, during the initial period of the esterification reaction, for example when the reaction is between about 0 to 25% complete, the reflux ratio may be set at between about 1 to 3 and either kept constant at that level or gradually increased up to a value of about 5. The percent completion of the esterification reaction is defined as the percent of the dicarboxylic acid charged to the reactor system which has been esterified. As the esterification reaction becomes more completed, the amount of water or alcoholic by-products produced per unit time decreases and the overhead condensate stream becomes progressively richer in the monohydroxy aromatic compound. Accordingly, the reflux ratio is to be increased to return the monohydroxy aromatic compound back into the reactor system to drive the esterification reaction towards completion. For the process in accordance with the present invention, the following profile for varying the reflux ratio is preferred:

| % Completion of Reaction | Reflux Ratio |
| --- | --- |
| 0-25 | 1-5 |
| 26-50 | 3-10 |
| 51-80 | 5-15 |
| 81-100 | 7-20 |

Most preferably, the reflux ratio is varied according to the following profile:

| % Completion of Reaction | Reflux Ratio |
| --- | --- |
| 0-25 | 2-5 |
| 26-50 | 5-7 |
| 51-80 | 7-10 |
| 81-100 | 10-15 |

It will be appreciated that the process of the present invention is distinct from a process where the reflux ratio in a simple batch distillation is increased as the separation there goes towards completion. In such a batch distillation, the objective is generally to obtain a pure product overhead. In contrast thereto, the present process seeks to maximize the removal of by-products of the esterification reaction to drive that reaction towards completion quickly and economically. It may be possible to obtain the results of the present process by the use of a constant but large reflux ratio, say 15 or 20, throughout the esterification reaction, but such a large reflux ratio would be extremely inefficient in terms of energies consumed, materials required, and size of the reactor system needed.

The amount of distillate to be removed from the reactor system should be about 0.01 to about 0.7 parts by weight per hour per part by weight of acid charged to the reactor. Preferably, the amount of distillate removed is about 0.07 to about 0.34 part by weight per hour per part by weight of acid charged.

The invention will now be further illustrated by the following examples.

EXAMPLE 1

The reaction apparatus consisted of a 500-gal. jacketed pressure reactor which was supplied with an agitator-baffle assembly. Hot oil was circulated through the jacket of the reactor to control the reaction temperature using an automatic temperature controller. The reactor was equipped with a distillation column, a shell and tube condenser, a reflux splitter and a reflux ratio controller combination. The distillation column was packed and the packing height was equivalent to approximately 15 theoretical plates. The distillate from the distillation column was collected in two receivers which were equipped with level indicators.

The reactor was charged with 454 parts by weight of 3:1 isophthalic acid to terephthalic acid mixture along with 1340 parts by weight of phenol. Two mole percent (based on the acid mixture) of antimony oxide catalyst was also charged to the reactor. The reaction system was closed and heated to a temperature of 255° C. where it was maintained through the entire reaction period. The distillate collection was started as the reaction temperature reached 230° C. by starting the coolant water flow into the condenser and setting the reflux ratio at 3:1. The distillate phenol-water mixture was collected at an average rate of 53 parts by weight per hour. The reflux ratio was systematically increased from a value of 3:1 in the beginning to 10:1 towards the end of reaction period as shown in Table I below along with the degree of esterification. Samples were collected from the reactor at regular intervals and were analyzed for acid number and phenol content. The acid number (AN) is defined as the amount in milligrams of potassium hydroxide needed to completely neutralize one gram of the sample by titration method. The corrected acid number (ANc) was calculated by using the following equation:

$$ANc = \frac{AN}{1 - Wp} \quad (1)$$

in which Wp represents the weight fraction of phenol in the sample. The degree of esterification (DE) was calculated by using:

$$DE = \frac{1 - \frac{(ANc)(Ma)}{2(56,100)}}{1 + Ec(ANc)\frac{Ma}{2(56,100)}} \times 100 \quad (2)$$

in which $$Ec = \frac{Me - Ma}{Ma},$$

and Ma and Me represent the molecular weights of the acid and of the ester, respectively.

TABLE I

| Time Internal (hrs) | Reflux Ratio | Degree of Esterification, % |
|---|---|---|
| 0–3 | 3:1 | 57 |
| 3–6 | 5:1 | 87.3 |
| 6–9 | 7:1 | 94 |
| 9–11 | 10:1 | 96.3 |

The pressure reached a maximum of 55 psig initially as the reaction temperature approached the temperature of 255° C. and decreased to 25 psig at the end of reaction.

EXAMPLE 2

The procedure described in Example 1 was repeated and the reactor was charged with 10.18 parts by weight of 3:1 isophthalic acid to terephthalic acid mixture and 35 parts by weight of phenol. Triethanol amine titanium chelate catalyst, available from the duPont Co. under its tradename Tyzor TE, was used in an amount equivalent to about 0.3 mole percent based on the acid mixture charged to the reactor. The reaction system was purged with nitrogen for 30 minutes. The reactor was heated to a temperature of 245° C. The temperature was maintained at 245° C. until the end of reaction which lasted 6 hours. The distillate correction started the water flow on the condenser when the internal reactor temperature reached 230° C. The reflux ratio was systematically increased from a value of 3:1 in the beginning to 11:1 towards the end of reaction as shown in Table II along with the degree of esterification.

TABLE II

| Time (hr.) | Reflux Ratio | Degree of Esterification, % |
|---|---|---|
| 1st | 3:1 | 42 |
| 2nd | 5:1 | 71 |
| 3rd | 7:1 | 83 |
| 4th | 9:1 | 92 |
| 5th | 11:1 | 97 |
| 6th | 11:1 | 99 |

The maximum pressure in the system of 52 psig was obtained as the final temperature of 245° C. was approached. The pressure decreased to 19 psig at the end of reaction. The distillate was collected at an average rate of 2.9 parts by weight per hour. An uncorrected acid number of 2.8 was obtained after 6 hours of reaction. The degree of esterification was calculated to be 99%.

EXAMPLE 3

The procedure of Example 2 was repeated, except that the pattern of changing the reflux ratio is as given in Table III below:

TABLE III

| Time (hrs.) | Reflux Ratio | Degree of Esterification, % |
|---|---|---|
| 1–3 | 3:1 | 0–50 |
| 4–7 | 5:1 | 50–77 |
| 8–12 | 10:1 | 77–93 |

A final degree of esterification of 93% was achieved in about 12 hours.

EXAMPLE 4

This example shows that good esterification can be also achieved by using a relatively large (~15 to 20) reflux ratio substantially constantly throughout the reaction. However, the disadvantage of such a process is largely in high energy costs involved in vaporizing and condensing a large stream for refluxing purpose, and the special equipment needed to effect the large amounts of heat transfer necessary. The reactor used for carrying out the esterification reaction was a 50-gal. stainless steel reaction (Model 50-E-150 DLTN) supplied by Bench Scale Equipment Company (Dayton, Ohio). The reactor was equipped with a 4-blade pitched turbine agitator, baffles, pressure gauge and rupture disc assembly. The reactor was electrically heated and equipped with a Honeywell #R7355C1082 DIALATROL temperature control system which included indication controllers, SCR power unit, thermocouple and circuit breakers. This reactor was fitted with Model A-1, 4" IPS stainless steel packed distillation column having 0.24" protruded packing distributors and packing support plates as per Bulletin 722 of Distillation Engineering Company (Livingston, N.J.). The packing height in the distillation column was approximately 3 feet. The distillation column was equipped with Model H-1 automatic reflux splitter and Model C-1 10 sq. ft., 316 SS, horizontal U-tube condenser also supplied by Distillation Engineering Co. The automatic reflux splitter was connected to Model F-3, 0-100:1, direct reading reflux ratio controller. This enabled the reflux ratio in the distillation column to be changed from a control panel. The overhead distillate from the distillation column was collected in a vessel equipped with a level indicator.

The reactor was charged with 210 parts by weight of phenol and 73.25 parts by weight of a mixture of 3:1 isophthalic acid to terephthalic acid. Two mole percent antimony oxide catalyst (based on the acid mixture) was also added to the reactor. After charging the reactants the reactor was purged with nitrogen for 30 minutes. After purging, the reaction system was sealed and heated to a final internal reactor temperature of 240° C. The internal reactor temperature was held constant at 240° C. throughout the reaction period with the help of an automatic temperature controller which controlled the electrical heat input to the reactor. The coolant water flow on the condenser, was started when the internal temperature in the reactor reached 230° C. As the condensation began the distillate was collected in the receiver after adjusting the reflux ratio to a desired value. A reflux ratio of at least 14:1 was used throughout the reaction time of 12 hours. The maximum reflux ratio used during the run was 20:1. The distillate which was a mixture of phenol and water was collected at an average rate of 10.4 parts by weight per hour over the reaction period. Table IV shows the variation of reaction pressure and degree of esterification with time.

TABLE IV

| Time (hr.) | Pressure (psig) | Degree of Esterification, % |
|---|---|---|
| 0 | 49 | — |
| 3 | 44 | 54.5 |
| 6 | 37 | 81 |
| 9 | 34 | 93 |
| 12 | 14 | 97.2 |

EXAMPLE 5

In this example the procedure of Example 4 was repeated. The reaction was carried out for the same length of time of 12 hours. The operation of the distillation column, i.e. the reflux ratios and the pressure, are summarized in Table V:

TABLE V

| Time Interval (hrs.) | Reflux Ratio | Pressure (psig.) | Degree of Esterification, % |
|---|---|---|---|
| 1st–4th | 0:1 | 46–43 | 0–51.3 |
| 5th–7th | 5:1 | 43–39 | 51.3–71 |
| 8th–10th | 10:1 | 39–23 | 71–82 |
| 11th–12th | 15:1 | 23–22 | 82–88.9 |

The distillate was collected at an average rate of 5.7 parts by weight per hour. A final degree of esterification of 88.9% was obtained after 12 hours. This example illustrates the point that when the initial reflux ratio is too low, the final degree of esterification that is achievable tends to be low.

EXAMPLE 6

The procedure of Example 4 was repeated except that the reflux ratio employed throughout the esterification reaction was zero. The final degree of esterification achieved after 12 hours was 84%.

The present application is being concurrently filed with applicant's co-pending applications Ser. No. 422,792 and Ser. No. 422,794, both for Process of Manufacturing Diaryl Esters of Dicarboxylic Acids, the disclosures of which are incorporated herein by reference.

The invention has been described with reference to particular and preferred embodiments thereof. It is to be understood that various changes and modifications can be made without departing from the spirit and scope of the invention.

What is claimed is:

1. A process for preparing esters which comprises reacting a monohydroxy aromatic compound with at least one dicarboxylic acid in a reactor having a distillation means, said acid being represented by the formula:

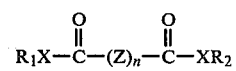

wherein X is oxygen or sulfur, Z is alkylene, —Ar— or —Ar—Y—Ar— where Ar is aromatic, Y is alkylene of 1 to 10 carbon atoms, haloalkylene, —O—, —SO—, —SO$_2$—, —SO$_3$—, —CO—,

or GN=, and G is alkyl, haloalkyl, aryl, haloaryl, alkylaryl, haloalkylaryl, arylalkyl, haloarylalkyl, cycloalkyl and halocycloalkyl, n is 0 or 1, and R$_1$ and R$_2$ are independently selected from the group consisting of hydrogen and lower alkyl, said reaction being conducted at a temperature between about 220° to about 300° C., continuously removing distillate from said distillation means at a rate of about 0.01 to about 0.7 parts by weight per hour per part by weight of acid charged to the reactor, said distillate including a by-product of said reaction comprising water and/or lower alkyl alcohol(s), and varying the reflux ratio in said distillation means during the course of the reaction according to a predetermined pattern.

2. A process according to claim 1 wherein said reflux ratio is periodically increased as the esterification reaction proceeds towards completion.

3. A process according to claim 1 wherein said reflux ratio is maintained between about 1 to about 20.

4. A process according to claim 1 wherein said reaction is conducted at a temperature about 235° C. to about 255° C.

5. A process according to claim 1 wherein said dicarboxylic acid is represented by the formula:

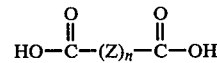

in which Z and n has the meaning as in claim 1.

6. A process according to claim 1 wherein said dicarboxylic acid comprises isophthalic acid, terephthalic acid, and mixtures of isophthalic and terephthalic acids.

7. A process according to claim 6 wherein said dicarboxylic acid comprises about 60 to 100 mole percent isophthalic acid and about 0 to 40 mole percent terephthalic acid.

8. A process according to claim 6 wherein said dicarboxylic acid comprises about 75 to 85 mole percent isophthalic acid and about 15 to 25 mole percent terephthalic acid.

9. A process according to claim 1 wherein the molar ratio of said monohydroxy aromatic compound to said dicarboxylic acid is from about 3:1 to about 10:1.

10. A process according to claim 9 wherein said molar ratio is from about 4:1 to about 8:1.

11. A process according to claim 1 wherein said monohydroxy aromatic compound is of the benzene or naphthalene series containing from 6 to about 20 carbon atoms.

12. A process according to claim 1 wherein said monohydroxy aromatic compound is phenol, a halophenol, or a nitro-phenol.

13. A process according to claim 1 wherein said reaction is conducted in the presence of a catalyst.

14. A process according to claim 13 wherein said catalyst is antimony oxide or an aliphatic ester of ortho titanic acid.

15. A process according to claim 13 wherein said catalyst is tetrabutyl titanate, tetraisopropyl titanate or tetraoctylene glycol titanate.

16. A process according to claim 2 wherein said reflux ratio is varied according to the following profile:

| % Completion of Reaction | Reflux Ratio |
| --- | --- |
| 0–25 | 1–5 |
| 26–50 | 3–10 |
| 51–80 | 5–15 |
| 81–100 | 7–20 |

17. A process according to claim 16 wherein said reflux ratio is varied according to the following profile:

| % Completion of Reaction | Reflux Ratio |
| --- | --- |
| 0–25 | 2–5 |
| 26–50 | 5–7 |
| 51–80 | 7–10 |
| 81–100 | 10–15 |

18. A process for preparing esters which comprises reacting a phenol with a dicarboxylic acid mixture made of about 75 to about 85 mole percent of an isophthalic acid and about 15 to about 25 mole percent of a terephthalic acid, the molar ratio of said phenol to said dicarboxylic acid mixture being from about 4:1 to about 8:1, said reaction being conducted in the presence of a catalyst and at a temperature about 220°–245° C. in a reactor having a distillation means, continuously removing distillate of said reaction through said distillation means at a rate of about 0.07 to about 0.34 part by weight per hour per part by weight of acid charged to the reactor, said distillate including a by-product of waid reaction comprising water and/or lower alkyl alcohol(s), and varying the reflux ratio in said distillation means according to the following profile:

| % Completion of Reaction | Reflux Ratio |
| --- | --- |
| 0–25 | 2–5 |
| 26–50 | 5–7 |
| 51–80 | 7–10 |
| 81–100 | 10–15 |

* * * * *